(12) United States Patent
Chuang (10) Patent No.: US 10,105,068 B2
(45) Date of Patent: Oct. 23, 2018

(54) PUMPLESS WEARABLE SPHYGMOMANOMETER

(71) Applicant: NANO-SECOND TECHNOLOGY CO., LTD., New Taipei (TW)

(72) Inventor: Pei-Sung Chuang, New Taipei (TW)

(73) Assignee: NANO-SECOND TECHNOLOGY CO., LTD., New Taipei (TW)

( * ) Notice: Subject to any disclaimer, the term of this patent is extended or adjusted under 35 U.S.C. 154(b) by 254 days.

(21) Appl. No.: 15/218,087

(22) Filed: Jul. 25, 2016

(65) Prior Publication Data

US 2017/0340210 A1 Nov. 30, 2017

(30) Foreign Application Priority Data

May 31, 2016 (TW) .............................. 105208156 U (51) Int. Cl.
*A61B 5/023* (2006.01)
*A61B 5/00* (2006.01)
*A61B 5/021* (2006.01)

(52) U.S. Cl.
CPC ............ *A61B 5/023* (2013.01); *A61B 5/0022* (2013.01); *A61B 5/02141* (2013.01);
(Continued)

(58) Field of Classification Search
CPC . A61B 5/022; A61B 5/02233; A61B 5/02241; A61B 5/023; A61B 5/02438
See application file for complete search history.

(56) References Cited

U.S. PATENT DOCUMENTS 4,320,767 A * 3/1982 Villa-Real ............... A61B 5/021
600/493
4,469,107 A 9/1984 Asmar et al.
(Continued)

FOREIGN PATENT DOCUMENTS

CN 203953630 11/2014
CN 203953630 U * 11/2014 ............. A61B 5/021
(Continued)

OTHER PUBLICATIONS

Office Action issued by United Kingdom Intellectual Property Office dated Feb. 9, 2017.

*Primary Examiner* — Meredith Weare
(74) *Attorney, Agent, or Firm* — Chieh-Mei Wang (57) ABSTRACT

A pumpless wearable sphygmomanometer includes a wearable element, a first fluid strip, a second fluid strip and a control module. A first side of the wearable element is for contacting with a wearer. The first and second fluid strips are arranged in parallel on the first side and spaced apart for a predetermined distance. The control module is disposed on the wearable element and includes a first pressure sensing element, a second pressure sensing element and a processing unit. The first and second pressure sensing elements communicate with the first and second fluid strips, respectively, and are configured to sense a first fluid pressure and a second fluid pressure in the first and second fluid strips, respectively. The processing unit is electrically connected to the first and second pressure sensing elements and configured to analyze a difference between the first fluid pressure and the second fluid pressure.

10 Claims, 6 Drawing Sheets

(52) U.S. Cl.
CPC .............. *A61B 5/681* (2013.01); *A61B 5/742* (2013.01); *A61B 5/7445* (2013.01); *A61B 2562/04* (2013.01)

(56) References Cited

U.S. PATENT DOCUMENTS

| | | | |
|---|---|---|---|
| 6,200,270 B1* | 3/2001 | Biehl | A61B 5/02427 600/490 |
| 9,205,019 B2* | 12/2015 | Ganske | A61B 17/1325 |
| 9,943,263 B2* | 4/2018 | Lee | A61B 5/681 |
| 2007/0197923 A1* | 8/2007 | Kishimoto | A61B 5/02141 600/490 |
| 2009/0099466 A1 | 4/2009 | Wong et al. | |
| 2010/0292586 A1 | 11/2010 | Rooke et al. | |
| 2010/0324430 A1 | 12/2010 | Inoue | |
| 2014/0296756 A1* | 10/2014 | Ganske | A61B 17/1325 601/151 |
| 2015/0335282 A1* | 11/2015 | Lee | A61B 5/681 600/499 |

FOREIGN PATENT DOCUMENTS

| | | | |
|---|---|---|---|
| EP | 0009789 | 9/1982 | |
| EP | 0606240 | 6/1998 | |
| EP | 0805649 | 9/2003 | |
| EP | 1125551 | 8/2006 | |
| EP | 1608261 | 11/2006 | |
| EP | 1779774 | 3/2014 | |
| FR | 2311525 | 12/1976 | |
| TW | 514511 | 12/2002 | |
| TW | I228408 | 3/2005 | |
| TW | I268439 | 12/2006 | |
| TW | M402699 | 5/2011 | |
| TW | M455472 | 6/2013 | |
| WO | WO 2013169014 A1 * | 11/2013 | ............. A61B 5/021 |

* cited by examiner

PUMPLESS WEARABLE SPHYGMOMANOMETER

TECHNICAL FIELD

The present invention relates to a sphygmomanometer, and more particularly to a pumpless wearable sphygmomanometer.

BACKGROUND

Development of the first blood pressure measuring method can date back to 1896. German pathologist von Recklinghausen found that in the process of measuring blood pressure by inflating and deflating an arm-wrapping airbag, the arm-wrapping airbag may generate a shockwave corresponding to the blood pressure. However, in the aforementioned blood pressure measuring method, a stethoscope is required. Today, with the development of electronic technology, shockwave can be sensed and measured by sensors instead of stethoscopes. That is, the airbag slowly releases its pressure, a sensor can be used to determine the point at which the shockwave sharply increases, which corresponds to the systolic blood pressure, and a point at which the shockwave starts to slow down, which corresponds to the diastolic blood pressure, thereby obtaining the blood pressure of a human subject.

Conventionally, electronic sphygmomanometer uses a pump to pressurize the airbag. Specifically, the systolic blood pressure and the diastolic blood pressure are sequentially measured by using the pump to press against the blood vessels thereby stopping blood flow in the vessels and then gradually release the air in the airbag. However, a conventional electronic sphygmomanometer requires a pump and a pressure release device, and thus resulting in a relatively large overall size. As wearable devices have become increasingly popular in recent years, the addition of a pump and a pressure release device would hinder the miniaturization of wearable sphygmomanometers.

SUMMARY

The present invention provides a pumpless wearable sphygmomanometer, which includes a wearable element, a first fluid strip, a second fluid strip and a control module. The first fluid strip is disposed on a first side of the wearable element. The first side is for contacting with a wearer. The second fluid strip is disposed on the first side. The first fluid strip and the second fluid strip are arranged in parallel and spaced apart for a predetermined distance from each other. The control module is disposed on the wearable element and includes a first pressure sensing element, a second pressure sensing element and a processing unit. The first pressure sensing element communicates with the first fluid strip and is configured to sense a first fluid pressure in the first fluid strip. The second pressure sensing element communicates with the second fluid strip and is configured to sense a second fluid pressure in the second fluid strip. The processing unit is electrically connected to the first pressure sensing element and the second pressure sensing element. The processing unit is configured to analyze a difference between the first fluid pressure and the second fluid pressure.

In an embodiment of the present invention, the first fluid strip is closer to the heart of the wearer than the second fluid strip is when the wearer wears the wearable element.

In an embodiment of the present invention, the control module further includes a housing, a first tubular member and a second tubular member. The housing is disposed on a second side of the wearable element. The first side and the second side are opposite to each other. The processing unit, the first pressure sensing element and the second pressure sensing element are disposed in the housing. The two terminals of the first tubular member are connected to the first pressure sensing element and the first fluid strip, respectively. The two terminals of the second tubular member are connected to the second pressure sensing element and the second fluid strip, respectively.

In an embodiment of the present invention, the aforementioned pumpless wearable sphygmomanometer further includes a display panel disposed in the housing and electrically connected to the processing unit. A display surface of the display panel is exposed from the housing.

In an embodiment of the present invention, the control module further includes a wireless transmission device disposed in the housing and electrically connected to the processing unit.

In an embodiment of the present invention, an accommodating groove is formed on the second side of the wearable element. The housing is disposed in the accommodating groove. The first fluid strip includes a first branch tube. The first branch tube passes through the wearable element from the first side, extends into the accommodating groove and is connected to the first tubular member. The second fluid strip includes a second branch tube. The second branch tube passes through the wearable element from the first side, extends into the accommodating groove and is connected to the second tubular member.

In an embodiment of the present invention, the accommodating groove has a bottom wall and a side wall connecting to and surrounding the bottom wall. A concave structure is formed on the side wall. An edge of the housing is engaged with the concave structure.

In an embodiment of the present invention, an engaging hole communicating with the concave structure is formed on the side wall of the accommodating groove. A projecting structure is formed on a side wall of the housing. The projecting structure is inserted into the engaging hole.

In an embodiment of the present invention, the first tubular member and the second tubular member are comprised of hard tubing. The first branch tube and the second branch tube are comprised of soft tubing.

In an embodiment of the present invention, the processing unit is further configured to issue an operating instruction, which includes: prompting the wearer to exert a force on the wearable element and thereby pressing against the first fluid strip and the second fluid strip; and prompting the wearer to gradually release the exerted force when both of the first fluid pressure and the second fluid pressure are greater than a predetermined value and the difference between the first fluid pressure and the second fluid pressure falls within a predetermined range.

In an embodiment of the present invention, the wearable element comprises a wrist band.

In summary, by utilizing the fluid strips to press against blood vessels in a wrist of the wearer, the pumpless wearable sphygmomanometer of the present invention can measure blood pressure of the wearer without the need of a pump. Consequently, the size of the pumpless wearable sphygmomanometer of the present invention may be reduced as pumps and the related components are no longer required. Further, because the pumpless wearable sphygmomanometer of the present invention employs two parallel fluid strips, a significant difference in measured pressures would be detected between the two fluid strips if the wrist of the wearer moves or is improperly pressed against. Therefore, once the pressure difference is greater than a predetermined value, it would be determined that the wearable pumpless sphygmomanometer of the present invention is operated under an abnormal condition; thus, measuring errors can be avoided. In addition, the pumpless wearable sphygmomanometer of the present invention may further display specific information such as notifying the wearer that the wrist has moved or has been improperly pressed against, so that the wearer may adjust the position of his/her wrist accordingly.

BRIEF DESCRIPTION OF THE DRAWINGS

The present invention will become more readily apparent to those ordinarily skilled in the art after reviewing the following detailed description and accompanying drawings, in which.

DETAILED DESCRIPTION OF PREFERRED EMBODIMENTS

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Please refer to FIGS. 1, 2, 3 and 4, which provides schematic views of a pumpless wearable sphygmomanometer according to an embodiment of the present invention. As shown, the pumpless wearable sphygmomanometer 100 of the present embodiment includes a wearable element 10, a control module 20, a first fluid strip 30 and a second fluid strip 40. The structure of each of the aforementioned element/component/device/member in the pumpless wearable sphygmomanometer 100 will be described hereafter.

Figure 1:
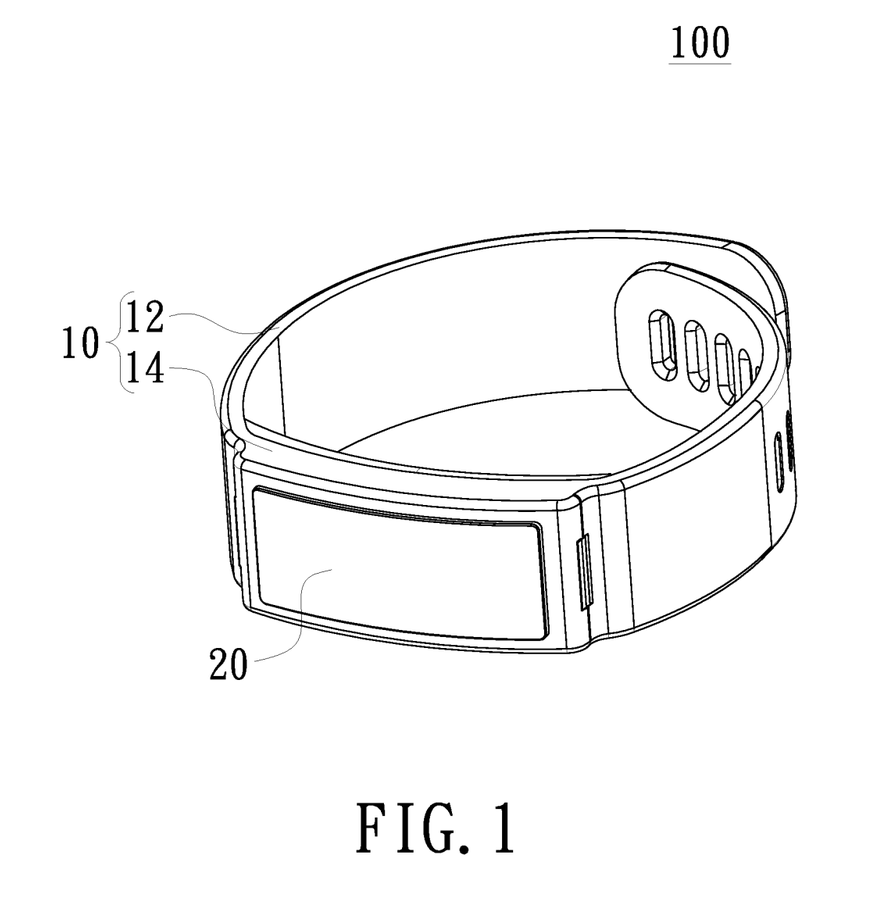
FIG. 1 is a perspective view of a pumpless wearable sphygmomanometer according to an embodiment of the present invention.
Figure 2:
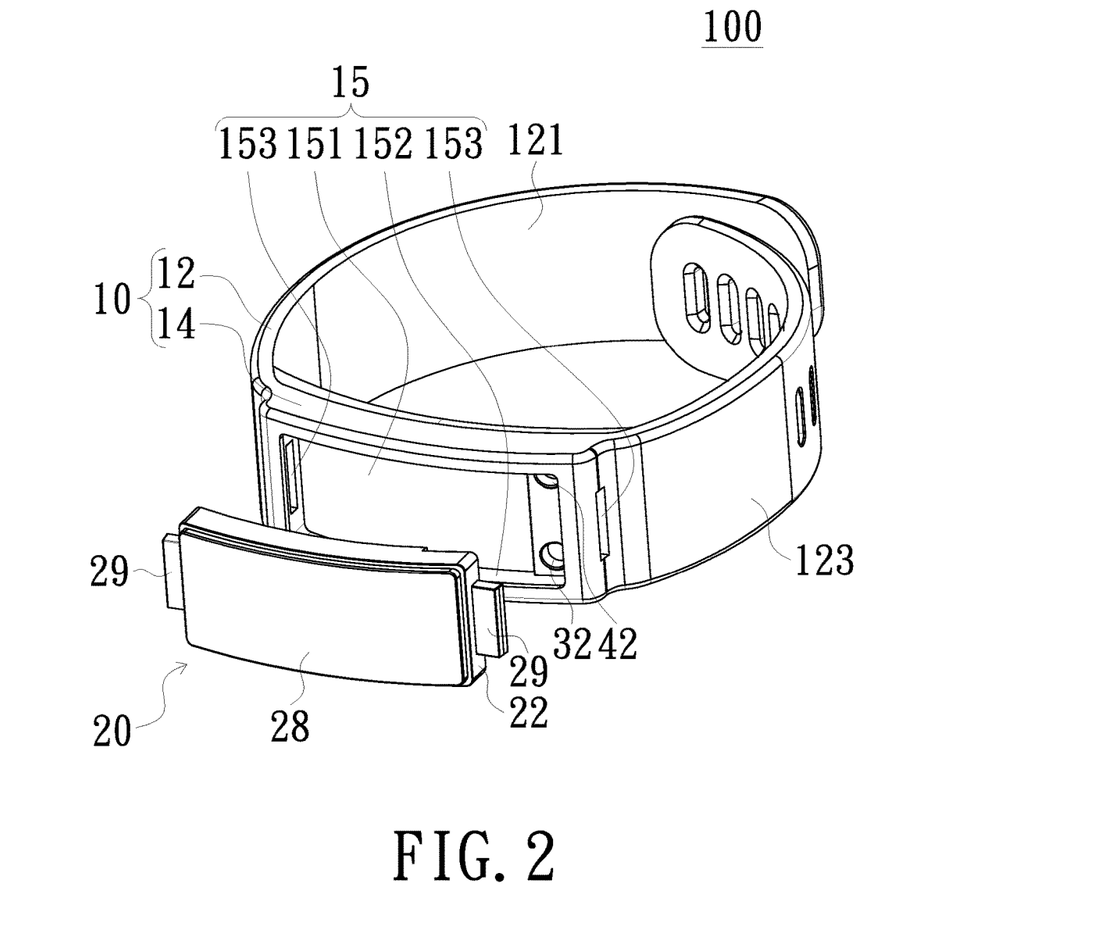
FIG. 2 is an exploded perspective view of the pumpless wearable sphygmomanometer of FIG. 1.
Figure 4:
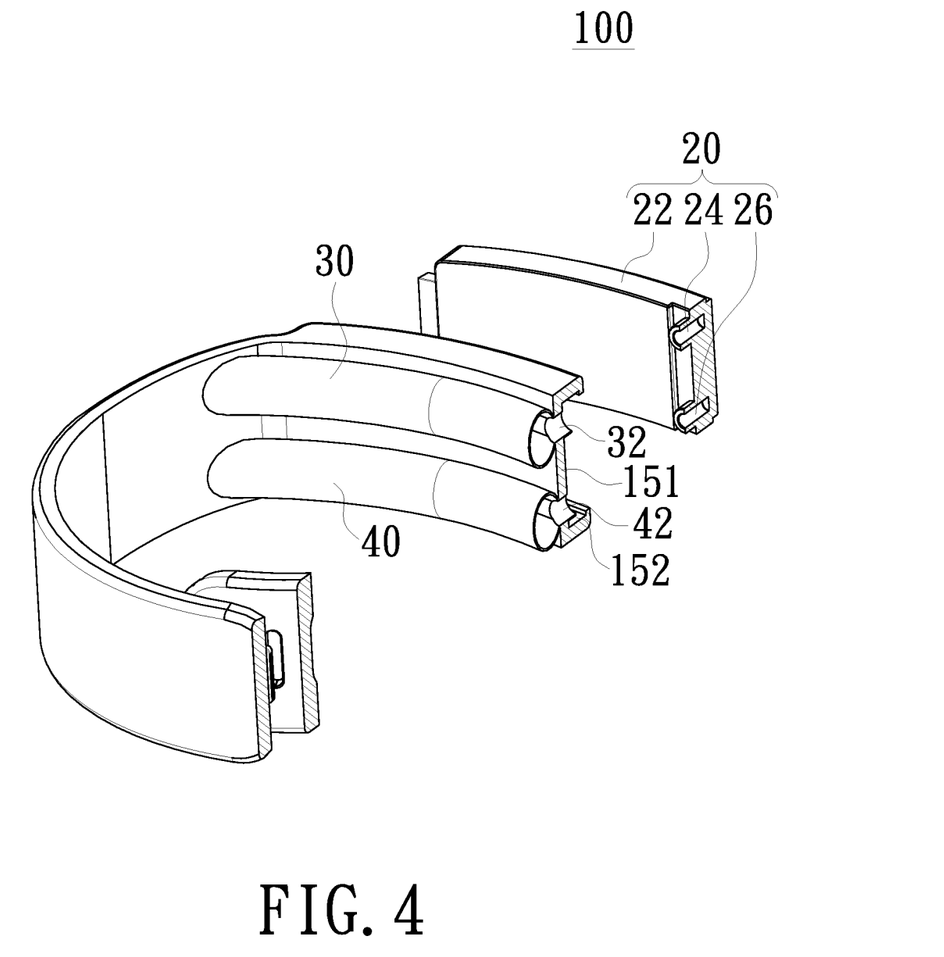
FIG. 4 is a cross-sectional view of the pumpless wearable sphygmomanometer of FIG. 1.

In the present embodiment, the wearable element 10 includes a wrist band 12. The wrist band 12 has an annular shape and may be worn or surround a wearer's wrist. The wearable element 10 has a first side 121 and a second side 123 opposite to the first side 121. Specifically, the first side 121 is the inner peripheral surface of the wearable element 10 and may contact with the wearer's wrist; and the second side 123 is the outer peripheral surface of the wearable element 10. In the present embodiment, the wearable element 10 may further include an accommodating portion 14. The accommodating portion 14 is disposed on the wrist band 12 and may be integrally molded with the wrist band 12 to form a one-piece structure. An accommodating groove 15 is formed on the front surface of the accommodating portion 14; that is, the accommodating groove 15 is formed on the second side 123 of the wearable element 12. The control module 20 is disposed in the accommodating groove 15, but the present invention is not limited thereto. In another embodiment, the accommodating portion 14 and the wrist band 12 are two separate structural components. Please refer to FIGS. 2 and 4. The accommodating groove 15 has a concave structure and includes a bottom wall 151 and a side wall 152 surrounding the bottom wall 151. As shown in FIG. 4, the concave structure is formed on the sidewall 152; that is, the cross-section of the side wall 152 forms a U-shaped structure. As shown in FIG. 2, two engaging holes 153 communicating with the aforementioned concave structure are formed on the side wall 152. In the present embodiment, the number/quantity of the engaging hole 153 is not limited to two. In another embodiment, the number/quantity of the engaging hole 153 may be one or more than two. The control module 20 may be engaged with the concave structure so as to be disposed in the accommodating groove 15. The structure of the control module 20 will be described later. In the present embodiment, although the wearable element 10 is worn or surrounds the wearer's wrist through the wrist band 12, but the present invention is not limited thereto. In another embodiment, the wrist band 12 may be replaced by an arm band or other band-like elements so that the wearable element 10 can be worn on a wearer's arm or other parts of the wearer's body.

Figure 3:
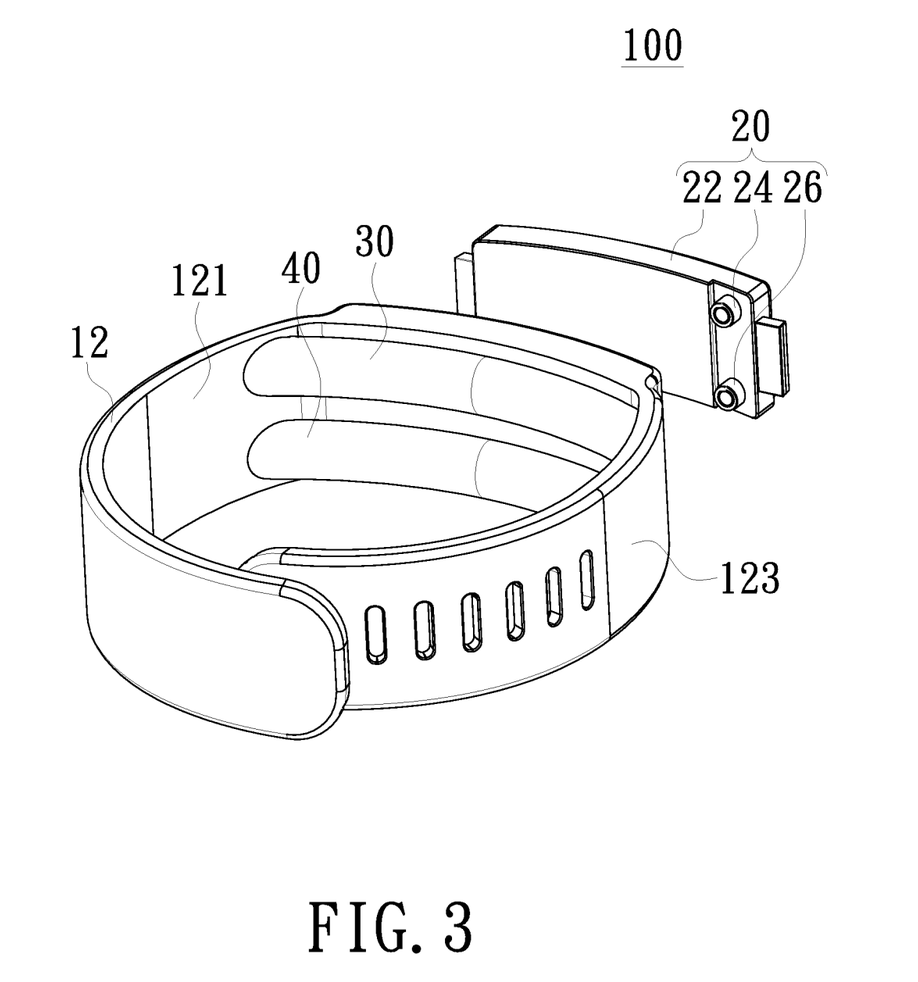
FIG. 3 is an exploded perspective view of the pumpless wearable sphygmomanometer of FIG. 1 from another viewing angle.

Please refer to FIGS. 2, 3 and 4. The first fluid strip 30 and the second fluid strip 40 are disposed on the back surface of the accommodating portion 14; that is, the first fluid strip 30 and the second fluid strip 40 are disposed on the first side 121 of the wearable element 10. In the present embodiment, the first fluid strip 30 and the second fluid strip 40 are arranged in parallel and spaced apart for a predetermined distance from each other. When the wearer wears the element 10, the first fluid strip 30 is relatively close to the wearer's core body and the second fluid strip 40 is relatively close to the wearer's hand; that is, the first fluid strip 30 is closer to the wearer's heart than the second fluid strip 40 is when the wearer wears the wearable element 10. As described above, both of the first fluid strip 30 and the second fluid strip 40 have strip structures and extend along the longitudinal direction of the wrist band 12; therefore, the first fluid strip 30 and the second fluid strip 40 can press against the same blood vessel in the wrist simultaneously when the wrist band 12 surrounds the wrist. Accordingly, blood pressure of the wearer can be measured based on the same blood vessel. In the present embodiment, the first fluid strip 30 and the second fluid strip 40 are made of soft tubing, which may be silicone materials having a diameter ranging from 5 millimeters (mm) to 6 mm; but the present invention is not limited thereto. In the present embodiment, the first fluid strip 30 and the second fluid strip 40 are filled with air. In another embodiment, the first fluid strip 30 and the second fluid strip 40 are filled with liquid. The first fluid strip 30 has a first branch tube 32. The second fluid strip 40 has a second branch tube 42. Both of the first branch tube 32 and the second branch tube 42 pass through the accommodating portion 14 from the first side 121 and extend into the accommodating groove 15.

Please refer to FIGS. 2 and 3. The control module 20 includes a housing 22, a first tubular member 24 and a second tubular member 26. The first tubular member 24 and the second tubular member 26 protrude from the back surface of the housing 22 and communicate with the interior and exterior of the housing 22. In the present embodiment, the first tubular member 24 and the second tubular member 26 are disposed on the same side of the housing 22, but the present invention is not limited thereto. In another embodiment, the first tubular member 24 and the second tubular member 26 are disposed on opposite sides of the housing 22, respectively; and correspondingly, the first branch tube 32 and the second branch tube 42 are disposed on the two opposite sides, respectively. Please refer to FIG. 2. Two projecting structures 29 are formed on the side walls of the two terminal surfaces of the housing 22. In the present embodiment, the number/quantity of the projecting structure 29 is not limited to two. In another embodiment, the number/quantity of the projecting structure 29 may be one or more than two. When the housing 22 of the control module 22 is mounted to the accommodating groove 15 of the accommodating portion 14, the edge of the housing 22 is engaged with the concave structure of the side wall 152 of the accommodating groove 15, and the projecting structures 29 are inserted into the respective engaging holes 153 of the accommodating groove 15. In the present embodiment, the number/quantity of the projecting structure 29 corresponds to that of the engaging hole 153, thereby fitting the control module 20 in the accommodating groove 15. Meanwhile, the first tubular member 24 and the second tubular member 26 are connected to the first branch tube 32 of the first fluid strip 30 and the second branch tube 42 of the second fluid strip 40 respectively, thereby allowing the control module 20 to communicate with the first fluid strip 30 and the second fluid strip 40. In the present embodiment, the first tubular member 24 and the second tubular member 26 are made of hard tubing; the first branch tube 32 and the second branch tube 42 are made of soft tubing; and the outer diameters of the first tubular member 24 and the second tubular member 26 are slightly greater than the inner diameters of the first branch tube 32 and the second branch tube 42, respectively. Therefore, sealing between the tubes is achieved by elasticity of the soft tubing when the first tubular member 24 and the second tubular member 26 are inserted into the first branch tube 32 and the second branch tube 42, respectively.

Figure 5:
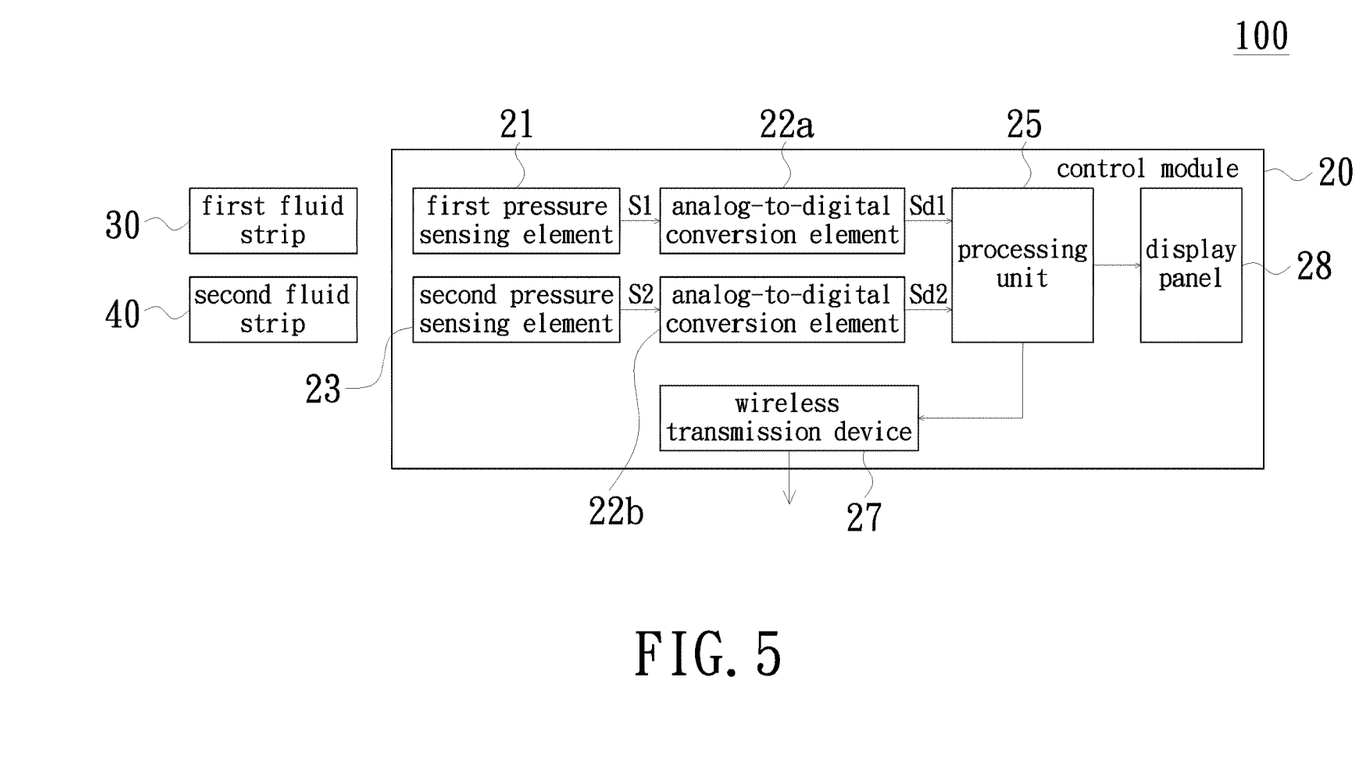
FIG. 5 is a block diagram of a system of a control module according to an embodiment of the present invention.

Please refer to FIG. 5, which is a block diagram of a system of the control module 20 according to an embodiment of the present invention. As shown, the control module 20 further includes a first pressure sensing element 21, a second pressure sensing element 23 and a processing unit 25. The processing unit 25 is electrically connected to the first pressure sensing element 21 and the second pressure sensing element 23. In addition, the control module 20 may further include analog-to-digital conversion elements 22a, 22b and a wireless transmission device 27. The first pressure sensing element 21, the second pressure sensing element 23, the processing unit 25 and the wireless transmission device 27 are disposed in the housing 22. The wireless transmission device 27 is electrically connected to the processing unit 25. In addition, the control module 20 may further include a display panel 28. The display panel 28 is electrically connected to the processing unit 25 and mounted onto the housing 22, and a display surface of the display panel 28 is exposed from the housing 22, thereby allowing information displayed on the display surface of the display panel 28 to be viewed by the wearer. The first pressure sensing element 21 communicates with the first fluid strip 30 through the first tubular member 24. The second pressure sensing element 23 communicates with the second fluid strip 40 through the second tubular member 26. When the wearer exerts a force on the wearable element 10 to cause the first fluid strip 30 and the second fluid strip 40 to press against the wearer's wrist, the pressures between the wearer's wrist and the first fluid strip 30 and the second fluid strip 40 cause fluid pressures to be generated in the first fluid strip 30 and the second fluid strip 40. The first pressure sensing element 21 and the second pressure sensing element 23 are configured to sense the fluid pressures in the first fluid strip 30 and the second fluid strip 40, and generate a first pressure signal S1 and a second pressure signal S2. The first pressure signal S1 and the second pressure signal S2 are then transmitted to the analog-to-digital conversion elements 22a, 22b, respectively. The analog-to-digital conversion elements 22a, 22b are configured to convert the first pressure signal S1 and the second pressure signal S2 into a first pressure digital signal Sd1 and a second pressure digital signal Sd2, and to transmit the first pressure digital signal Sd1 and the second pressure digital signal Sd2 to the processing unit 25, respectively. The processing unit 25 is configured to compare the first pressure digital signal Sd1 and the second pressure digital signal Sd2 to a predetermined value. Specifically, when it is determined that both of the first pressure digital signal Sd1 and the second pressure digital signal Sd2 are higher than the predetermined value, the processing unit 25 issues specific information, such as prompting the wearer to gradually release the exerted force, to the display panel 28. The processing unit 25 is further configured to compare between the first pressure digital signal Sd1 and the second pressure digital signal Sd2. Once the wearer gradually releases the exerted force, the pressures of the first fluid strip 30 and the second fluid strip 40 against the blood vessel are gradually released, blood starts to flow through the blood vessel and pulses of the heart start to transmit through the blood, and thereby blood pressure of the wearer can be measured. It is understood that systolic blood pressure refers to the blood pressure at which the pulse of blood pressure starts to sharply increase, and diastolic blood pressure refers to the blood pressure at which the pulse of blood pressure starts to slow down. When the pulse of blood pressure is transmitted to the pumpless wearable sphygmomanometer 100 of the present embodiment, because the first fluid strip 30 is closer to the wearer's heart than the second fluid strip 40 is, the time point at which the first fluid strip 30 detects blood pressure would be earlier than that at which the second fluid strip 40 detects so. Therefore, by comparing the blood pressures obtained from the first fluid strip 30 and the second fluid strip 40, the timings at which the pulse of blood pressure starts to sharply increase or slow down may be determined. Namely, by setting a predetermined value and once a pressure difference between the first fluid strip 30 and the second fluid strip 40 reaches the predetermined value (e.g., the pressure measured by the second fluid strip 40 is 40% higher than the pressure measured by the first fluid strip 30 within a certain period as in one embodiment), it is determined that the pulse of blood pressure starts to sharply increase; and the pressure measured from the first fluid strip 30 corresponds to the systolic blood pressure. It is to be understood that the aforementioned value 40% is for an exemplary purpose only; the value is adjustable in response to actual requirements and the value is not limited in the present invention.

Alternatively, if the pressure difference between the first fluid strip 30 and the second fluid strip 40 is close to zero, it is determined that the pulse of blood pressure starts to slow down; and the pressure measured from the first fluid strip 30 corresponds to the diastolic blood pressure. Thereafter, the measured systolic and diastolic blood pressures are displayed on the display panel 28 for the wearer to view. In addition, the measured systolic and diastolic blood pressures may be transmitted to a mobile device (e.g., a mobile phone, not shown) via the wireless transmission device 27 and recorded on the mobile device. In addition, the measured systolic and diastolic blood pressures may be further transmitted to Cloud or a medical service system from the mobile device. In another embodiment, the control module 20 may not include the display panel 28. Correspondingly, the processing unit 25 is configured to directly transmit the operating instructions (e.g., prompting the wearer to start exert a force or start to release the exerted force) to a mobile device via the wireless transmission device 27; and the measured systolic and diastolic blood pressures are directly transmitted to the mobile device via the wireless transmission device 27 for the wearer to view.

Figure 6:
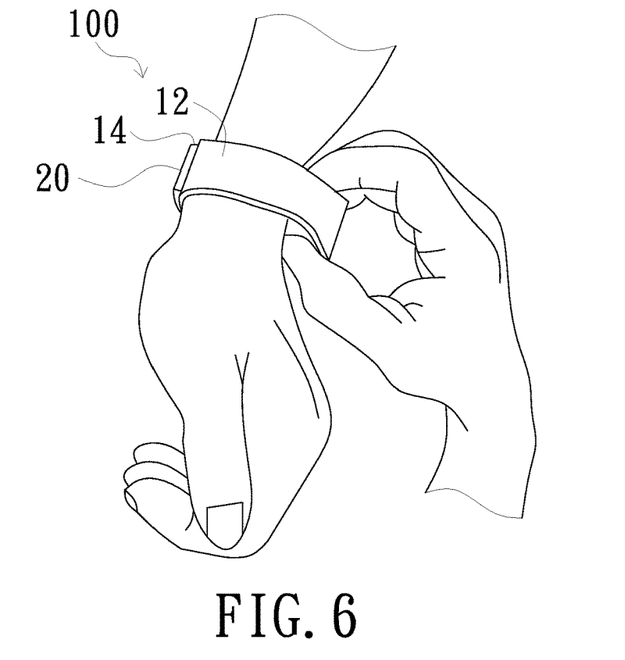
FIGS. 6 and 7 are schematic diagrams illustrating an operation of a pumpless wearable sphygmomanometer according to an embodiment of the present invention.
Figure 7:
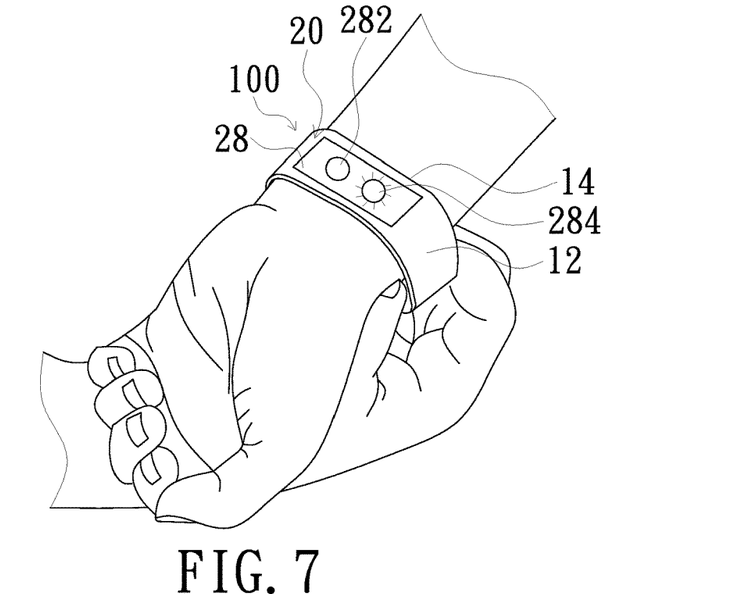

Please refer to FIGS. 6 and 7, which are schematic diagrams illustrating an operation of a pumpless wearable sphygmomanometer according to an embodiment of the present invention. As shown in FIG. 6, the first fluid strip 30 and the second fluid strip 40 disposed on the back surface of the accommodating portion 14 are pressed against the wearer's wrist. Then, the processing unit 25 controls the display panel 28 to display a specific operating instruction such as prompting the wearer to exert a force on the wearable element 10, thereby pressing against the first fluid strip 30 and the second fluid strip 40. In one embodiment, for example, when a red icon 282 on the display panel 28 starts to flash, the wearer exerts a force on the wrist band 12 so as to press the first fluid strip 30 and the second fluid strip 40 against blood vessels in the wearer's wrist. Then, the first pressure sensing element 21 and the second pressure sensing element 23 senses the fluid pressures in the first fluid strip 30 and the second fluid strip 40 and transmit the measured pressure values to the processing unit 25, respectively. Thereafter, the processing unit 25 compares the pressure values measured from the first fluid strip 30 and the second fluid strip 40 to a predetermined value (e.g., higher than 180 mmHg; specifically, 210 mmHg in one embodiment; and the present invention is not limited thereto). When it is determined that both of the pressure values measured from the first fluid strip 30 and the second fluid strip 40 are higher than the predetermined value and the pressure difference between the two measured pressure values is within a predetermined range, the processing unit 25 controls the display panel 28 to display a specific operating instruction such as prompting the wearer to gradually release the exerted force. For example, in one embodiment as shown in FIG. 7, when a green icon 284 on the display panel 28 starts to flash, the wearer gradually releases the exerted force and the wearable sphygmomanometer starts to measure the blood pressure. Once the systolic and diastolic blood pressures of the wearer are measured, the measured systolic and diastolic blood pressures are displayed on the display panel 28.

In summary, by utilizing the fluid strips to press against blood vessels in a wrist of the wearer, the pumpless wearable sphygmomanometer of the present invention can measure the blood pressure of the wearer without the need of a pump. Consequently, the size of the pumpless wearable sphygmomanometer of the present invention may be reduced as pumps and the related components are no longer required. Further, because the pumpless wearable sphygmomanometer of the present invention employs two parallel fluid strips, a significant difference in measured pressures would be detected between the two fluid strips if the wrist of the wearer moves or is improperly pressed against. Therefore, once the pressure difference is greater than a predetermined value, it would be determined that the pumpless wearable sphygmomanometer of the present invention is operated under an abnormal condition; thus, measuring errors can be avoided. In addition, the pumpless wearable sphygmomanometer of the present invention may further display specific information such as notifying the wearer that the wrist has moved or has been improperly pressed against, so that the wearer may adjust the position of his/her wrist accordingly.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A pumpless wearable sphygmomanometer, comprising:
   a wearable element;
   a first fluid strip, disposed on a first side of the wearable element, wherein the first side is for contacting with a wearer;
   a second fluid strip, disposed on the first side, wherein the first fluid strip and the second fluid strip are arranged in parallel and spaced apart for a predetermined distance; and
   a control module, disposed on the wearable element and comprising:
      a first pressure sensing element, communicating with the first fluid strip and configured to sense a first fluid pressure in the first fluid strip;
      a second pressure sensing element, communicating with the second fluid strip and configured to sense a second fluid pressure in the second fluid strip; and
      a processing unit, electrically connected to the first pressure sensing element and the second pressure sensing element, wherein the processing unit is configured to analyze a difference between the first fluid pressure and the second fluid pressure and to issue an operating instruction, and the operating instruction comprises:
         prompting the wearer to exert a force on the wearable element and thereby pressing against the first fluid strip and the second fluid strip; and
         prompting the wearer to gradually release the exerted force when both of the first fluid pressures and the second fluid pressure are greater than a predetermined value and, concurrently the difference between the first fluid pressure and the second fluid pressure falls within a predetermined range.

2. The pumpless wearable sphygmomanometer according to claim 1, wherein the first fluid strip is closer to a heart of the wearer than the second fluid strip is when the wearer wears the wearable element.

3. The pumpless wearable sphygmomanometer according to claim 1, wherein the control module further comprises:
   a housing, disposed on a second side of the wearable element, wherein the second side is opposite to the first side, and the processing unit, the first pressure sensing element and the second pressure sensing element are disposed in the housing;
   a first tubular member, wherein two terminals of the first tubular member are connected to the first pressure sensing element and the first fluid strip, respectively; and
   a second tubular member, wherein two terminals of the second tubular member are connected to the second pressure sensing element and the second fluid strip, respectively.

4. The pumpless wearable sphygmomanometer according to claim 3, further comprising a display panel, disposed in the housing and electrically connected to the processing unit, wherein a display surface of the display panel is exposed from the housing.

5. The pumpless wearable sphygmomanometer according to claim 3, wherein the control module further comprises a wireless transmission device, disposed in the housing and electrically connected to the processing unit.

6. The pumpless wearable sphygmomanometer according to claim 3, wherein an accommodating groove is formed on the second side of the wearable element, the housing is disposed in the accommodating groove, the first fluid strip comprises a first branch tube, the first branch tube passes through the wearable element from the first side, extends into the accommodating groove and is connected to the first tubular member, and the second fluid strip comprises a second branch tube, the second branch tube passes through the wearable element from the first side, extends into the accommodating groove and is connected to the second tubular member.

7. The pumpless wearable sphygmomanometer according to claim 6, wherein the accommodating groove has a bottom wall and a side wall connecting to and surrounding the bottom wall, a concave structure is formed on the side wall, and an edge of the housing is engaged with the concave structure.

8. The pumpless wearable sphygmomanometer according to claim 7, wherein an engaging hole communicating with the concave structure is formed on the side wall of the accommodating groove, a projecting structure is formed on a side wall of the housing, and the projecting structure is inserted into the engaging hole.

9. The pumpless wearable sphygmomanometer according to claim 6, wherein the first tubular member is inserted into the first branch tube, and the second tubular member is inserted into the second branch tube.

10. The pumpless wearable sphygmomanometer according to claim 1, wherein the wearable element comprises a wrist band.

* * * * *